(12) United States Patent
Metcalfe et al.

(10) Patent No.: US 8,449,619 B2
(45) Date of Patent: May 28, 2013

(54) HIP STEM INSTRUMENT WITH RELEASABLE CONNECTION

(75) Inventors: Nick James Theophilus Metcalfe, Chipping Norton (GB); Robert John Andrew Bigsby, South Wales (GB)

(73) Assignee: Biomet UK Limited (GB)

( * ) Notice: Subject to any disclaimer, the term of this patent is extended or adjusted under 35 U.S.C. 154(b) by 1440 days.

(21) Appl. No.: 10/559,151

(22) PCT Filed: Jun. 4, 2004

(86) PCT No.: PCT/GB2004/002367
§ 371 (c)(1),
(2), (4) Date: Jun. 19, 2006

(87) PCT Pub. No.: WO2004/108024
PCT Pub. Date: Dec. 16, 2004

(65) Prior Publication Data
US 2006/0241625 A1 Oct. 26, 2006

(30) Foreign Application Priority Data
Jun. 6, 2003 (GB) .................................. 0313137.2

(51) Int. Cl.
*A61F 2/32* (2006.01)
(52) U.S. Cl.
USPC .................. 623/22.11; 623/22.42; 623/22.43; 403/289

(58) Field of Classification Search
USPC ................. 623/22.11, 22.42, 22.43; 403/289, 403/302, 325, 328, 329, DIG. 14
See application file for complete search history.

(56) References Cited

U.S. PATENT DOCUMENTS

| 5,288,161 | A | * | 2/1994 | Graves et al. | 403/324 |
| 5,688,281 | A | | 11/1997 | Cripe et al. | |
| 5,720,750 | A | | 2/1998 | Koller et al. | |
| 5,888,211 | A | | 3/1999 | Sanders | |
| 5,906,644 | A | | 5/1999 | Powell | |
| 6,159,216 | A | | 12/2000 | Burkinshaw et al. | |
| 6,193,759 | B1 | * | 2/2001 | Ro et al. | 623/23.28 |
| 6,656,225 | B2 | * | 12/2003 | Martin | 623/20.12 |
| 6,977,000 | B2 | * | 12/2005 | Vanasse et al. | 623/22.42 |
| 2001/0035652 | A1 | * | 11/2001 | Wada et al. | 292/128 |
| 2001/0051831 | A1 | | 12/2001 | Subba Rao et al. | |
| 2002/0020041 | A1 | | 2/2002 | Newman et al. | |

FOREIGN PATENT DOCUMENTS

| EP | 0 619 097 A | 10/1994 |
| FR | 2 796 267 A | 1/2001 |
| GB | 1 375 934 A | 12/1974 |

* cited by examiner

*Primary Examiner* — David Isabella
*Assistant Examiner* — Randy Shay
(74) *Attorney, Agent, or Firm* — Harness, Dickey

(57) ABSTRACT

A surgical device includes a first portion and a second portion. The first and second portions are releasably connected together by cooperating first and second formations. The first formation may be formed on the first portion. The second formation includes a resilient arm which is formed on the second portion and engages the first formation on the first portion. The resilient arm may be integrally formed with the second portion.

9 Claims, 1 Drawing Sheet

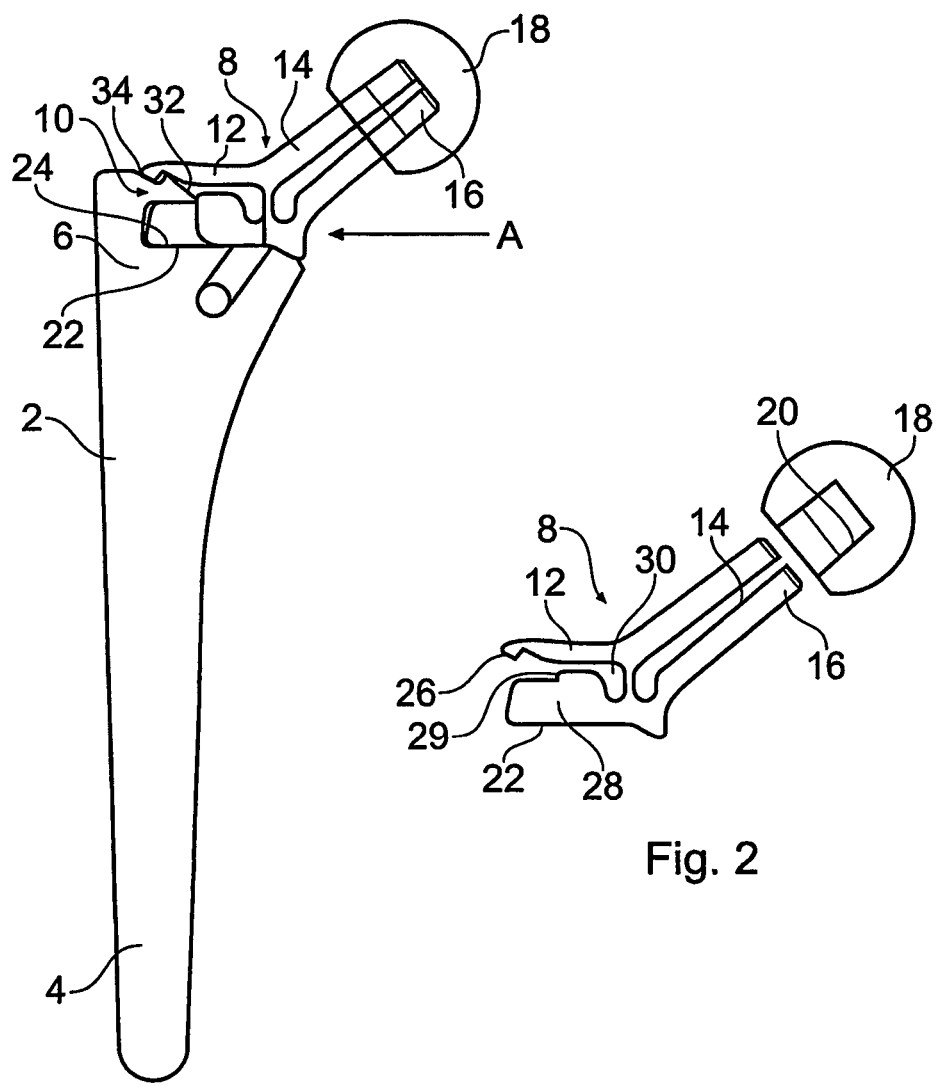

HIP STEM INSTRUMENT WITH RELEASABLE CONNECTION

FIELD

This invention relates to a surgical device and particularly relates to a device having two main components which are interconnected by a "snap-fit" connection.

INTRODUCTION

One goal of hip reconstruction is to attempt to reproduce the normal kinematics of the hip by recreating the functional geometry of the acetabulum and proximal femur. This can greatly influence the outcome of the operation, restoring normal muscle function, gait and ultimately the longevity of the implant.

In one exemplary replacement hip surgery a femoral component is inserted into a prepared femur. The femoral component may have a stem portion which projects into the femoral canal of the prepared femur and may have an integral or separate modular head of substantially spherical shape. The ball-like head of the femoral component may be received within an acetabular cup component which is implanted in the patient's hip socket, i.e., the acetabulum. The acetabular cup may have a substantially hemi-spherical bearing surface for movement of the ball head of the femoral component during action of the joint. The acetabular cup may be implanted into the prepared hip socket either with or without cement. Cementless types of acetabular cup may be secured in the prepared bone by a press fit or can be directly screwed in place or otherwise secured in place, for example by indirect means, e.g., by the use of separate bone screws passing through apertures provided in the acetabular cup. Generally, the femoral stem may be formed of metal and the ball head may be formed of metal or of a ceramic material.

In some exemplary designs of hip prostheses the material of the bearing surface of the acetabular cup, is of the same material as that of the ball head, e.g., for a ceramic head a ceramic bearing surface is provided (a so-called ceramic-on-ceramic prosthesis) and for a metal head a metal bearing surface is provided (a so-called metal-on-metal prosthesis). In some other exemplary designs, the acetabular bearing surface may be formed of polyethylene and the acetabular cup may either be provided with a polyethylene inner liner or the acetabular cup may be a single component made entirely from polyethylene.

The connection between the femoral stem and the femur may be cemented or cementless. Depending on which type of connection is used, an appropriate broach and/or file may be used to enlarge the femoral canal. For a cementless connection, the file is of substantially the same dimensions as the femoral stem which is to be implanted, whereas if the connection is cemented, the file is slightly oversized relative to the femoral stem. Once the femoral canal has been enlarged sufficiently to accommodate it, the femoral stem is implanted. Then a series of trial femoral heads, which have bearing surfaces offset laterally and/or displaced relative to the femoral stem to differing degrees, may be attached to the femoral stem. This "trial reduction" procedure is used to select the most appropriate femoral head for a particular patient.

The applicant uses a modified procedure in which the broach or file itself, rather than the actual femoral stem, is used with a variety of trial femoral heads in a trial reduction procedure. This allows the surgeon to assess stability of the joint and leg length, prior to selecting the definitive implant.

One exemplary method of altering stability and leg length includes providing a modular femoral head having a range of neck lengths. The head center may be moved either longer or shorter than the standard zero position. This will increase or decrease femoral offset and thus alter tissue tension, stability, but at the same time will also affect leg length. Another exemplary method includes using an increased offset stem, which will increase tissue tension by lateralising the femur, without increasing leg length. Both methods can be assessed at the trial reduction stage.

In many conventional techniques, the interconnection between the femoral head and the femoral stem (or the broach or file in the case of the applicant's existing procedure) comprises a pin formed on the femoral stem, file or broach and a corresponding socket formed on the femoral head. Such an arrangement provides good lateral alignment, but may not prevent displacement of the femoral head along a longitudinal axis of the femoral stem, broach or file. This "pistoning" effect may make it more difficult to select an appropriate femoral head and tends to complicate the trial reduction procedure.

SUMMARY

A surgical device can include a first portion and a second portion, the first and second portions being releasably connected together by cooperating first and second formations. The second formation can include a resilient arm on the second portion which engages the first formation on the first portion.

The first formation may be integrally formed with the first portion. The first formation may comprise a recess or projection.

The second formation may be integrally formed with the second portion. It is particularly advantageous to form the first formation integrally with the first portion and/or the second formation with the second portion, because the less components there are in a surgical tool, the easier it is to sterilise. It will be appreciated that by forming the cooperating formations integrally with the first and second portions, the number of separate components is reduced to a minimum and the surgical tool is particularly easy to sterilize.

In one example, the recess or projection may be formed on the resilient arm and adapted to engage the first formation. The recess or projection may be formed at a free end of the resilient arm. The second portion may be at least partially bifurcated.

In another example, the resilient arm may form a fork of the bifurcated part of the second portion. The first formation may be received between forks of the bifurcated part of the second portion. The first portion may be provided with a first planar guide surface which engages a second planar guide surface on the second portion. An abutment may be provided, for example on the first or second planar guide surface, which abutment limits the relative movement between the first and second portions.

The first portion may be adapted to connect, one at a time, to a plurality of alternative second portions.

The surgical device may comprise a hip prosthesis for replacing a head of a femur. The first portion may comprise the stem of a prosthesis, and the second portion is the same shape as a neck of the prosthesis. The second portion may be adapted to receive a prosthetic femoral head.

Alternatively, the first formation may comprise a surgical tool. The second portion may comprise a detachable handle. The first portion may comprise a drill bit, broach, file or rasp.

The first portion may comprise an annular ridge formed around the circumference of the surgical tool. The resilient arm may be biased radially inwardly towards the surgical tool and may engage over the ridge.

The resilient arm may be arcuate and curve at least partially around the circumference of the surgical tool.

The second portion may comprise an adaptor to which a plurality of alternative femoral heads can be connected. In an alternative embodiment, a plurality of adaptors of different lengths and/or shapes may be provided for use with alternative femoral heads, or a common femoral head, such that adjustment of the femoral head relative to the femoral stem is provided by the adaptor, rather than, or as well as, by the femoral head itself.

A method for attaching a first implant portion to a second implant portion includes providing a femoral stem defining a longitudinal axis. The femoral stem may include a first formation and a first planar guide surface arranged on a proximal portion thereof. An adapter may be advanced along the first planar guide surface, the adapter including a second formation. The first and second formations may be selectively connected in an engaged position.

According to other features, a second planar guide surface defined on the adapter may be slidably advanced along the first planar guide surface. A projection defined on the second formation may be slidably advanced along a leading surface defined on the first formation. The second formation may be resiliently deflected in a direction generally away from the first planar guide surface. The projection may locate into a ridge defined on the femoral stem in the engaged position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 shows an exemplary femoral file, adaptor and trial femoral head in an assembled condition; and FIG. 2 shows the exemplary adaptor and trial femoral head of FIG. 1 in a disassembled condition.

DETAILED DESCRIPTION OF THE PREFERRED EMBODIMENT

The following description of the embodiment(s) is merely exemplary in nature and is in no way intended to limit the invention, its application, or uses. Moreover, while the description below is directed to a hip prosthesis, the same may be directed to an implant for any portion of the body.

FIGS. 1 and 2 illustrate an exemplary surgical device comprising a femoral broach or file 2 comprising a file portion or stem 4 which tapers outwardly towards an enlarged fixing portion 6. An adaptor 8 may be connected to the fixing portion 6 by cooperating formations 10, 12. The adaptor 8 may be provided with a shaft 14 which tapers towards a free end 16 of the adaptor 8. A trial femoral head 18, having a socket 20 which tapers inwardly towards its base, may be received closely on the shaft 14.

A planar guide surface 22 may be formed on the adaptor 8 and rests on a corresponding planar guide surface 24 formed on the fixing portion 6 of the femoral file 2.

The second formation 12 may be integrally formed with the adaptor 8 and comprises a resilient arm having, at its free end, a projection 26. The adaptor 8 may be bifurcated at its end opposite to free end 16, such that the resilient arm comprises a first fork. The portion 28 of the adaptor 8, on which the planar guide surface 22 may be formed, comprises the second fork. A recess 30 may be defined between the resilient arm and the portion 28. An abutment 29 may be formed on the adaptor 8 and projects into the recess 30.

The first formation 10 comprises a projection with a sloping leading surface 32 and a ridge 34 which may be formed in an end surface of the fixing portion 6.

During implantation of a prosthetic hip joint, the proximal end of the femur is prepared and the femoral canal can be enlarged by means of the broach or file 2. When the broach or file is being used to enlarge the femoral canal a handle (not shown) may be attached to the fixing portion 6.

When the required dimensions of the femoral canal have been achieved, the file 2 may be left in place and the handle may be detached. The adaptor 8 may then be offered up to the file 2, such that the planar guide surface 22 rests on the planar guide surface 24 of the file 2 and the first formation 10 may be received in a mouth of the recess 30. The adaptor 8 may then be pushed in the direction A towards the first formation 10, so that the projection 26 rides up the leading surface 32 and drops into the ridge 34. At this instant, a leading edge of the first formation 10 comes into contact with the abutment 29, so that the adaptor 8 is firmly connected to the file 2. A trial reduction can then be carried out by offering up various trial femoral heads 18 have different offsets or having sockets 20 of different depths until an appropriate femoral head has been selected.

Finally, the file 2 may be removed from the femoral canal and an appropriate femoral prosthesis may be assembled with the selected femoral head and implanted into the femur.

In an alternative embodiment not illustrated, a plurality of alternative trial adaptors 8 are provided, which may for example have different lengths of shaft 14. An appropriate adaptor 8 may then be selected either for use with a common femoral head 18, or for use with one of a plurality of different femoral heads. During the trial reduction, the easy interconnection of each adaptor 8 with the file 2, simply by means of pushing the cooperating formations 10, 12 together to make the connection and pulling them apart to break the connection, enables rapid selection of an appropriate adaptor.

It is readily apparent that as the formation 10 is integrally formed with the file 2 and the resilient arm 12 is integrally formed with the adaptor 8, the overall number of components are minimized and the surgical device as a whole is convenient to sterilize.

The fixing portion 6 of the file 2 and the bifurcated region of the adaptor 8 can be made using a variety of known techniques. In one example, these components may be cut from solid blocks of material such as by using a hot wire cutter.

Various materials can be used to form the adaptor 8, such that the resilient arm 12 has sufficient resilience to be repeatedly connected to and disconnected from the file 2. Custom (registered trade mark) 455 stainless steel and Aubert & Duval X15TN stainless steel, for example, are particularly good materials for use with a surgical device in accordance with the present disclosure.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

The invention claimed is:

1. A hip stem instrument comprising: a first portion substantially in the form of a stem with a first formation attached to the first portion and a second portion formed as a single piece having a body extending from a first end to a second end, the second end defining a resilient arm, the first and second portions being releasably and directly connected together by cooperation of the first formation and the second end, the first formation having a first ramp surface and being attached to the first portion, the resilient arm having a second ramp surface, the second end being at least partially bifurcated and forming first and second forks, the resilient arm forming the first fork of the second portion, and the first formation being received between the resilient arm and the second fork of the second portion, wherein the resilient arm moves from a first position when the first and second ramp surfaces initially engage, through a range of second positions corresponding to the second ramp surface slidably and progressively ramping along the first ramp surface, to a third position wherein the second ramp surface clears the first ramp surface and drops into a ridge provided on the first formation such that the first formation is received and firmly connected between the resilient arm and the second fork of the second portion, the first portion having a first planar guide surface and the second fork of the second portion having a second planar guide surface, wherein the first and second planar guide surfaces slidably engage while the resilient arm moves through the first, second, and third positions, the first planar guide surface being substantially transverse to a longitudinal axis of the first portion.

2. A hip stem instrument comprising:
a first portion and a second portion selectively moveable between connected and disconnected positions, the first portion including a first formation, the second portion formed as a single piece having a body portion extending between first and second ends, wherein the second end is bifurcated and forms first and second forks, the first fork forming a resilient arm, the first formation having a first sloping leading surface, and an adjacent ridge and one of a recess and a projection, the resilient arm having a complementary second sloping leading surface and a corresponding other one of the recess and projection of the first formation; and
wherein the resilient arm is offset from the body portion of the second portion, the resilient arm selectively moveable between an engaged position with the first formation in the connected position and a disengaged position with the first formation in the disconnected position, wherein the resilient arm moves from a first position when the first and second sloping leading surfaces initially engage, through a range of second positions corresponding to the second sloping leading surface slidably and progressively ramping along the first sloping leading surface, to a third position wherein the second sloping leading surface clears the first sloping leading surface and drops into the ridge provided on the first formation such that the first formation is received and firmly connected between the resilient arm and the second fork of the second portion in the connected position, the first portion having a first planar guide surface and the second fork of the second portion having a second planar guide surface, wherein the first and second planar guide surfaces slidably engage while the resilient arm moves through the first, second, and third positions, the first planar guide surface being substantially transverse to a longitudinal axis of the first portion.

3. The hip stem instrument of claim 2, wherein the first formation is integrally formed with the first portion.

4. The hip stem instrument of claim 2, wherein the other one of the recess and projection is formed at a free end of the resilient arm.

5. The hip stem instrument of claim 2, wherein the second fork further comprising an abutment which limits the relative movement between the first and second portions, the first formation engaging the abutment in the connected position.

6. The hip stem instrument of claim 5, in which the first portion comprises a surgical tool.

7. The hip stem instrument of claim 6, wherein the first portion comprises one of a drill bit, a broach, a file and a rasp.

8. The hip stem instrument of claim 2, wherein the second portion comprises an adaptor to which a femoral head can be connected.

9. A hip stem instrument comprising:
a stem including a proximal end and the distal end, the proximal end having a first planar surface and a first formation extending from the proximal end above the first planar surface, the first formation including a ramp and a ridge; and
an adapter configured to be releasably and directly connected to the proximal end of the stem, the adapter formed as a single piece having a body portion extending between a first end and a second end, the first end being bifurcated and including a first fork in the form of a resilient arm and a second fork, the resilient arm being offset from the body portion and including an end projection, the second fork including a second planar surface and an abutment opposite to the second planar surface, wherein the projection of the resilient arm is configured to ride up the ramp and drop into the ridge, while the second planar surface contacts the first planar surface and the first formation is received between the resilient arm and the second fork to connect the adapter to the stem with a firm connection, wherein the first planar surface is substantially transverse to a longitudinal axis of the stem.

* * * * *

UNITED STATES PATENT AND TRADEMARK OFFICE
CERTIFICATE OF CORRECTION

| | |
|---|---|
| PATENT NO. | : 8,449,619 B2 |
| APPLICATION NO. | : 10/559151 |
| DATED | : May 28, 2013 |
| INVENTOR(S) | : Metcalfe et al. |

It is certified that error appears in the above-identified patent and that said Letters Patent is hereby corrected as shown below:

In the Claims:

Column 5, line 54, Claim 2, before "an" delete "and".

Signed and Sealed this
Third Day of September, 2013

Teresa Stanek Rea
*Acting Director of the United States Patent and Trademark Office*